United States Patent
Ashe

(10) Patent No.: US 6,528,991 B2
(45) Date of Patent: *Mar. 4, 2003

(54) MAGNETIC POSITION MEASUREMENT SYSTEM WITH FIELD CONTAINMENT MEANS

(75) Inventor: Westley Ashe, Milton, VT (US)

(73) Assignee: Ascension Technology Corporation, Burlington, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/897,083

(22) Filed: Jul. 3, 2001

(65) Prior Publication Data

US 2003/0011359 A1 Jan. 16, 2003

(51) Int. Cl.$^7$ ................................................ G01B 7/30
(52) U.S. Cl. ................................................ 324/207.17
(58) Field of Search ....................... 324/207.17, 207.12, 324/207.14, 207.16, 207.23, 207.24, 207.25, 207.26; 336/84 R, 84 C, 84 M; 128/899; 600/424

(56) References Cited

U.S. PATENT DOCUMENTS 6,246,231 B1 * 6/2001 Ashe ...................... 324/207.17

* cited by examiner

Primary Examiner—Walter E. Snow
(74) Attorney, Agent, or Firm—H. Jay Spiegel

(57) ABSTRACT

A magnetic field position and orientation measurement system contains, confines and re-directs the magnetic field from one or more transmitters such that the fields are attenuated in areas outside of the operating volume in areas where metallic objects are commonly found. An attenuator made of a highly permeable material such as ferrite or mumetal may be placed on top of a conductive plate. The permeable attenuator may be as thin as 0.001 inches. on top of the permeable attenuator, a transmitter system is placed including at least three transmitters. In one embodiment, the transmitter consists of a PC board carrying the transmitter. The transmitter system, the permeable attenuator and the conductive plate, where used, may only be from ½ inch to ⅝ of an inch in thickness combined. The permeable attenuator may have a flat, planar configuration. Alternatively, it may be made to resemble, in cross-section, a cake pan having a flat central region with uplifted peripheral edges. Alternatively, the permeable attenuator may have a generally flat configuration with peripheral edges that taper outwardly from the top surface thereof to the bottom surface thereof with the taper making an angle with the bottom surface in the range of, preferably, 30° to 85°. The conductive plate is optional.

33 Claims, 6 Drawing Sheets

MAGNETIC POSITION MEASUREMENT SYSTEM WITH FIELD CONTAINMENT MEANS

BACKGROUND OF THE INVENTION

The present invention relates to a magnetic position measurement system with field containment means. The concept of using transmitting and receiving components with electromagnetic coupling is well known with respect to biomechanics and medical diagnostics, wherein a sensor assembly is mounted on a point of interest and the position of the point is determined relative to a fixed transmitter. This information is then used by computing systems to precisely show the relative motions of the points in question, which, in the medical sense, allows instruments to be precisely located in a human body with respect to the body and each other. This allows new, advanced methods of surgery and diagnostics to be performed.

When conductive materials are present, which is often the case on, below, or near an operating table, they generate eddy current fields, which distort the received magnetic field waveform, which distorts the output of the system unless the system utilizes some distortion reducing or compensating technique. When permeable materials are present, they bend and otherwise distort the magnetic field, with effects similar to conductive materials. In a surgical theater, both conductive and permeable materials are present in substantial quantities. They are a major component of many operating tables, surrounding equipment such as carts and equipment, and are present in the movable spot lamps used to illuminate the surgical field. Many operating tables have many degrees of positional and angular freedom to allow optimal placement of the surgical field relative to the surgeon, and are designed to be extremely stable and sturdy while supporting a heavy human body. As a result of these requirements, the tables contain numerous mechanisms allowing fore, aft, up, down, sideways, roll, and tilt motions. These mechanisms are physically robust and typically fabricated from steel, so that they have substantial field distortion characteristics. Shapes may include screws, rack and pinion gears, or scissors type actuators. The table surface may be one piece, or may be divided into several sections, with each section capable of motion relative to the other sections, to allow a body to be flexed such that various stresses and relative anatomical positions are optimal for a particular surgical or diagnostic procedure. The installed bases of operating tables are extremely diverse in design, and as the tables are often in service for many decades, there are many vendors, with each vendor carrying a number of different operating table designs. This poses a significant problem for magnetic position tracking systems which are used in a critical surgical environment. The operating volume for the tracker is typically within the body which lies on top of the table. This means that the tracking system is operating in close proximity to the metallic structures on, under, and around the table. The magnetic fields are distorted by these structures, which may result in large errors in the reported magnetic sensor position. The large diversity in table designs makes it impossible to predict the severity of distortion experienced on a given table. This is an unacceptable condition for a surgical environment. Attempts to compensate for these degrading effects have been made with varying degrees of effectiveness.

One method already employed is to map the entire operating volume each time the system is used. This is very time consuming and expensive, as potentially thousands of points must be taken in a precise manner if the distortion is severe and the operating volume large. It is also unreliable since during a surgical or diagnostic procedure, the table geometry is often changed which changes the relation of the table metallic structures relative to the tracking system, thereby requiring a new map if errors cannot be tolerated. Instruments and diagnostic equipment are also introduced and removed from the vicinity of the tracking system, thus rendering a map ineffective. Also, for severe distortion, a map may become totally ineffective, as the system may, at two different physical sensor spatial points, determine the sensor to be at the same position. In this case, the output data is of minimal use.

Another known method commonly described in prior art is to use AC fields over a conductive ground plane. The ground plane attenuates the magnetic field below the plane to nearly zero, which has the benefit of making the system insensitive to metallic objects below the plane. In the case of a dipole transmitter, the "method of images" is used to compute the theoretical magnetic field vectors over the plane, which are then used to provide sensor position. This method has drawbacks. One is that near the ground plane, the magnetic field intensity is nearly zero, and the vector crossing angles are degraded, which seriously reduces system performance with respect to accuracy and noise. The net result is that the sensor must be kept a few inches above the plane. Also, the dipole must be located some distance from the ground plane in order to reduce signal losses and degraded vector crossing angles within the operating volume. For a 1 cubic foot volume, the bottom of the transmitter must be about 2 inches above the plane for acceptable performance. To compute the height at which a patient must be elevated if lying on the transmitter, the thickness of the transmitter must be added to this 2 inch figure. Transmitter size is determined by required signal level within the operating volume. Sensor coil size for minimally invasive surgical applications is about 1 mm×5 mm in cross-section, which is very small. The requirement for precise, low noise operation at the extreme edges of the volume requires that a relatively large magnetic field magnitude be present in order to induce sufficient signal in the small coils. Transmitter size is largely dictated by how much field it must output. Since the transmitter is typically a cube, to obtain sufficient signal within a 1 cubic foot volume with a small receiver coil, the practical transmitter dimensions are on the order of 2 inches per side. We can now see that the effective transmitter assembly in this prior art teaching, including the ground plane, is 4 inches thick. In a surgical environment, the patient must be elevated to levels which a surgeon may find uncomfortable. In addition, extra padding may become necessary if the patient must lie flat on the table. Both the transmitter and the padding must be secured to the table. In short, the configuration is cumbersome and may not allow the patient to be positioned in an optimal manner.

Placing the transmitter above the operating volume is not desirable as it will potentially interfere with the surgical field. Also, as the transmitter is placed further from the ground plane, and if the dimensions of the ground plane are fixed to be a square of about 18 inches on a side, the ground plane becomes ineffective at reducing the effects of metallic objects near the operating volume. The metal housings of the surgical lighting equipment will have a greater distorting effect in the upper portions of the operating volume, as they are closer to both the transmitter and receiver. Equipment used during the procedure, including the operating table, will cause potentially life threatening distortion, which is an unacceptable condition.

Position determination depends on relative vector magnitudes from the transmitter coils. Distortion effects may again be removed by using a process such as mapping. As the magnitudes of the transmitted magnetic vectors from the transmitter coils become more similar, a given fixed amount of error in their determination will result in an increased error in position output. Again, considering the limiting case, if the magnitudes become equal then position determination is not possible. This combined effect of reduced angle of transmitted vector intersection and reduced difference in transmitted vector magnitudes is known to those skilled in the art as geometric dilution. Use of a conductive ground plane under the transmitter will cause geometric dilution. The severity of the geometric dilution is increased as the transmitter becomes closer to the ground plane, and is also increased as the receiver becomes further from the transmitter. Geometric dilution generally imposes a practical limit on how close the transmitter of a magnetic tracking system may be placed to a conductive ground plane. For a 1 cubic foot motion box, geometric dilution approaches unacceptable levels if the transmitter is placed closer than 2 inches from an infinite extent conductive ground plane. Geometric dilution is also present in non-dipole transmitter configurations, and the effects of its presence are similar.

The following prior art is known to Applicant:

U.S. Pat. No. 4,849,692 to Blood discloses a method of eliminating eddy current distortion effects, which are generated by conductive objects, such as the stainless steel table surface, and in other objects having large surface areas. The distortion effects of permeable metals are not addressed by this system. This means that steel structures in, around, and under the operating region of the system will distort the received magnetic fields and degrade system performance. In addition, large, thick sheets of conductive metals such as Aluminum have eddy current decay times which can exceed 200 milliseconds. If the system uses 3 time division multiplexed transmit axes plus one period where all axes are off in order to compensate for the earth's field, as described in the preferred embodiment, this means that the update rate is ¼*(200 mS)=1.25 Hz. This is unacceptably slow for many applications.

U.S. Pat. No. 5,767,669 to Hansen, et al. describes methods for eddy current field compensation without the need to compensate for the Earth's field effects. This system has no provision for reducing the effect of nearby permeable metals, nor does it address the drawback of requiring a slow update rate while operating near large, thick sheets of highly conductive metals.

U.S. Pat. No. 5,600,330 to Blood discloses a non-dipole loop transmitter-based magnetic tracking system. This system shows reduced sensitivity to small metallic objects in the operating volume, as the field from the smaller object will fall off as $1/r^3$ with r being the received distance from that object, while the field from the larger transmitting loops will fall off as $1/r^2$, which yields a reduced effect from the small metallic object. Large sheets of metal, however, can have an effective loop area larger than the magnetic transmitter loops, which diminishes this advantage in field fall off rate, which has the general effect of making the system quite sensitive to large metallic objects.

Also, metallic objects parallel to and near the transmitter loops produce very large eddy current magnitudes which reduces the signal level within the operating volume. In order to reduce the effects of metallic objects near the transmitter in this system, the transmit coils must be placed some distance away from the ground plane in order to reduce signal loss, which occurs when a loop of wire gets close to a conducting ground plane parallel with the plane of the loop. In the case of the planar transmitter configuration in this system, a planar ground plane may be placed some distance below the transmit coils. For zero distance, the magnetic field reduction within the operating volume is nearly total, so one must find a compromise between effective transmitter thickness, defined as the total thickness of the transmit coils, ground plane, and spacing between them, and signal loss. Also, due to the fact that the ground plane eddy current loop area is large with respect to a single transmit coil area, there is an additional degrading effect as the sensor gets further from the transmitter. The ground plane current distribution is similar no matter which transmit coil is operating. This means that the ground plane eddy current field vectors will be similar also. Since the field at any point within the operating volume is the vector sum of transmit coil field minus ground plane eddy field, and the ground plane field effective radius is larger than the transmit coil radius, we can see that the further we get from the plane of the transmitter, the more the field is determined by the ground plane currents. The net effect is that the vectors from the 3 transmit coils are less distinct, which makes the system more sensitive to noise and metallic distortion, as the system uses differences in the vector magnitudes and directions to determine position. As these differences become small, a small change on one of the vectors can result in a large apparent change of receiver position.

U.S. Pat. No. 5,752,513 to Acker, et al. depicts a system which is a subset of the system described by Blood '330, and operation in all respects is identical with respect to non-dipole transmitter properties and metal sensitivity.

U.S. Pat. No. 5,550,091 to Fukuda, et al. depicts a system using a so-called "Helmholtz" arrangement to produce a controlled field within the operating volume. One disadvantage of this system is its bulk, requiring the operating volume to be surrounded by the "Helmholtz" coil assembly. A second disadvantage of this system is that, when placed upon a metallic object such as a steel table, the magnetic field from the transmit coils will be distorted inside of the operating volume.

U.S. Pat. No. 5,640,170 to Anderson discloses a method of positioning a dipole over a specially constructed spiral over a ground plane. The dipole transmitter in this system must be located over the center of the spiral ground plane assembly, which makes patient placement more difficult in a clinical setting, as this placement may interfere with the surgical field during certain procedures. The benefit of this method is that it is possible to locate the transmitter closer to the ground plane, and one does not need to use the "method of images" to solve for position, but the disadvantage of transmitter location over the spiral/ground plane assembly is very similar to the case of a ground plane only.

U.S. Pat. No. 5,198,768 to Keren depicts a surface coil array for use in NMR applications. The system does not determine position, and does not utilize any methods for reducing the effect of nearby metallic objects.

The present invention represents a radical departure from the prior art relating to such transmitting and receiving position and orientation devices insofar as it is capable of satisfying the requirement of insensitivity to metallic objects under and adjacent to the transmitter assembly without exhibiting the disadvantages of signal degradation.

SUMMARY OF THE INVENTION

The present invention relates to embodiments of a magnetic field position and orientation measurement system with means for substantially containing, confining and re-directing the magnetic field from one or more transmit elements such that the fields are attenuated in areas outside of the operating volume in areas where metallic objects are commonly found.

The present invention relates to devices for measuring the position of receiving antennae relative to transmitting antennae using magnetic fields. Particularly, although not exclusively, such devices are for measuring that position in six degrees of freedom, namely, motion or translation in three coordinate directions (location) and/or rotational motion above three coordinate axes (orientation), location being commonly defined by X, Y, and Z linear coordinates referring to three mutually perpendicular directions and orientation being commonly described by pitch, roll and azimuth angular coordinates above three mutually perpendicular axes usually coincident with the three mutually perpendicular directions. The number of transmitting axes multiplied by the number of receiving axes is at least equal to a desired number of measured degrees of freedom.

The present invention includes the following interrelated objects, aspects and features:

(1) In the preferred embodiment, a flux containment means is used to redirect the flux vectors such that they are enhanced inside of the sensor operating volume and decreased under and adjacent to the transmitter plane, which reduces the sensitivity of the system to metals under and near the transmitter. The flux vectors from the transmitters are distorted by the flux containment means in a stable and repeatable manner, thus it is possible to precisely and repeatably characterize the distorted field. Once the precise vector distribution from the transmitter assembly is known, solution of position and orientation from a receiving means is a straightforward task to those familiar with the magnetic position tracking art. One reliable method for accomplishing this vector characterization is to utilize finite element analysis to compute the magnetic field vectors from the transmitter. Another reliable method is to employ one of several so-called mapping techniques which are known processes to those familiar with the art.

(2) The preferred embodiment of the present invention teaches a method for creating a representative magnetic transmitter assembly with reduced sensitivity to metallic objects under and adjacent to the operating volume of the system. The preferred embodiment also reduces the geometric dilution effects of a conductive ground plane to levels which are no longer of concern. This reduction in geometric dilution yields a system which is substantially less sensitive to distortion caused by metallic objects within the operating volume while maintaining insensitivity to metallic objects below the transmitter and reduced sensitivity to objects adjacent to the operating volume. The transmit means may include a number of wire loops, solenoids, or permanent magnets arranged in convenient shapes and locations for determining the position of the receiver within the volume. While 3-axis transmitters may be used in the present invention, it is also feasible to use transmitter means consisting of three transmitters having any angular or spatial relationship therebetween provided that relationship is known and quantified. The thickness of the permeable attenuator is generally chosen such that the saturation flux density of the attenuator material is not exceeded. Some ferrites have a saturation flux density of a few hundred Gauss, while annealed iron materials have about 15,000 Gauss. Mu metal has a saturation flux density of about 7,000 Gauss. Analyzing the attenuator thickness combined with a transmitter means using finite element analysis will produce values for flux density within the attenuator. For relatively thin attenuators, flux density is inversely proportional to thickness, so if the density is seen to be at or near saturation, the attenuator can be made thicker. In other cases, the transmitter excitation may be reduced. If the flux density within the attenuator exceeds the saturation value, the shielding effect of the attenuator is reduced. In some applications in which cost or weight is placed at a premium, operation with a saturated attenuator may still be acceptable, as the attenuator will still exhibit reduced sensitivity to metallic objects adjacent to and below the transmitter compared to a non attenuator equipped system.

(3) The present invention achieves the requirement for a system which may be placed upon a surface of any extent and composition without degrading the accuracy of the position readings from a sensor located within the desired operating volume. It achieves this goal for both AC and DC transmitter excitations, which is not at all possible using prior art ground plane based compensation methods. It achieves this goal while significantly increasing the magnetic field intensity within the operating volume, which is not possible using prior art ground plane based compensation methods. It also avoids the problem of geometric dilution which is introduced when a conductive ground plane is placed near the transmitter.

(4) In the preferred embodiment of the present invention, the permeable attenuator is made of a highly permeable but substantially non-conductive material such as ferrite or mumetal. In the preferred embodiment, the thickness of the permeable layer when made of ferrite is from 0.05 inches to 0.25 inches whereas use of mumetal can reduce the thickness to below 0.01 inches. Of course, these ranges are merely exemplary. The thickness of the permeable attenuator is generally chosen such that the saturation flux density of the attenuator material is not exceeded. Some ferrites have a saturation flux density as low as a few hundred Gauss, while annealed iron materials have about 15,000 Gauss. Mu metal has a saturation flux density of about 7,000 Gauss. Analyzing the attenuator thickness combined with a transmitter means using finite element analysis will produce values for flux density within the attenuator. For relatively thin attenuators, flux density is inversely proportional to thickness, so if the density is seen to be at or near saturation, the attenuator can be made thicker. In other cases, the transmitter excitation may be reduced. If the flux density within the attenuator exceeds the saturation value, the shielding effect of the attenuator is reduced. In some applications in which cost or weight is placed at a premium, operation with a saturated attenuator may still be acceptable, as the attenuator will still exhibit reduced sensitivity to metallic objects adjacent to and below the transmitter compared to a non-attenuator equipped system. The conductive plate, preferably made of an aluminum alloy, may be from 3/16 of an inch to 1/4 inch in thickness. In certain applications, it may be more efficient to employ the permeable attenuator without a conductive plate. In the case of DC transmitter excitation, for example, the additional shielding effect of the conductive plate is reduced to insignificant levels. In certain other cases, the performance benefit of the conductive plate may be outweighed by reduced mass, thickness, or other system considerations. In cases such as these, the additional mechanical support provided by the conductive plate may also be unnecessary, so that the conductive plate is removed entirely. In cases where the conductive plate provides a performance benefit to the system, this benefit is always of a secondary nature, with the primary performance enhancement arising from the permeable attenuator. Where mumetal is employed in the permeable layer, the thickness of the conductive plate may be reduced because the thickness is not chosen for mechanical support. Above the permeable attenuator, transmitter means are located. In one embodiment, the transmitter may consist of a PC board with the transmitter etched thereon.

(5) In certain applications, it may be more efficient to employ the permeable attenuator without a conductive plate. In the case of DC transmitter excitation, for example, the additional shielding effect of the conductive plate is reduced to insignificant levels. In certain other cases, the performance benefit of the conductive plate may be outweighed by reduced mass, thickness, or other system considerations. In cases such as these, the additional mechanical support provided by the conductive plate may also be unnecessary, so that the conductive plate is removed entirely. In cases where the conductive plate provides a performance benefit to the system, this benefit is always of a secondary nature, with the primary performance enhancement arising from the permeable attenuator.

(6) If a conductive object in the regions adjacent to or under the transmitter is subjected to an AC magnetic field, an eddy current will be induced in the object. This induced eddy current will produce a magnetic field component, which, by the addition of vectors, will combine with and distort the normal metal-free magnetic field near the object. The magnitude of this parasitic eddy field is proportional to the magnitude of the AC field near the conductive object.

(7) It is thus seen that if the field vectors in the operating volume above the transmitter assembly remain constant in magnitude and direction while the field magnitude in the regions adjacent to and under the transmitter assembly are reduced, then metallic objects in those regions will have a proportionally reduced distorting effect on the field in the operating volume above the transmitter assembly. If the field magnitude in the operating volume above the transmitter assembly is increased while the field magnitudes in the regions adjacent to and under the transmitter assembly remain constant, the distortion reducing effect is similar. Accordingly, the ratio of the magnetic field amplitude in the operating region above the transmitter assembly over that of the regions adjacent to and under the transmitter assembly may be used to predict sensitivity to metallic objects. A similar description applies to ferromagnetic distortion effects when the distorting objects are located in the regions adjacent to and below the transmitter assembly.

(8) If the relative magnetic distortion sensitivity values of a single transmit coil in the configuration such as is shown in FIG. 13, can be established as a normal value, then a relative distortion sensitivity figure of merit Ma for objects adjacent to the operating volume may be defined where Ma equals (the field of the system depicted in FIG. 2 in the region above the transmitter assembly) divided by (the field of the system depicted in FIG. 5 in the region above the transmitter assembly) divided by (the field of the system illustrated in FIG. 2 in the region adjacent the transmitter assembly) divided by (the field of the system in the configuration of FIG. 5 in the region adjacent the transmitter assembly). The system depicted in FIG. 11 will have a sensitivity figure of merit of 1 in that FIG. 11 will, for example, be chosen as the reference system.

(9) Similarly, for comparison of objects below the transmitter assembly, we can define a term Mb which equals (the field of the system of FIG. 2 in the region above the transmitter assembly) divided by (the field of the system illustrated in FIG. 5 in the region above the transmitter assembly) divided by (the field of the system of FIG. 2 below the transmitter assembly) divided by (the field of the system of FIG. 5 in the region below the transmitter assembly). Using the figures of merit Ma and Mb, several different configurations can be evaluated to determine likely relative sensitivities to metallic objects in the regions adjacent to and below the transmitter assembly.

Accordingly, it is a first object of the present invention to provide a magnetic position measurement system with field containment means.

It is a further object of the present invention to provide such a system wherein a permeable attenuator is provided.

It is a still further object of the present invention to provide such a system wherein the substantially high permeability, substantially non-conductive attenuator has upturned peripheral edges.

It is a still further object of the present invention to provide such a system wherein the substantially high permeability, substantially non-conductive attenuator has peripheral edges that taper downwardly from a top surface thereof to a bottom surface thereof.

It is a still further object of the present invention to provide such a system wherein transmitter means are mounted above the permeable attenuator.

It is a still further object of the present invention to provide a system for quantitatively measuring the position of receiving antennae relative to transmitting antennae without encountering the disadvantages that accrue from sensitivity to metallic objects directly below the transmitter.

It is a yet further object of the present invention to create a system that is insensitive to metallic objects at or below the plane of the transmitter.

It is a still further object of the present invention to provide such a system which avoids loss of transmit field intensity within the intended operating volume.

It is a still further object of the present invention to provide such a system which is not significantly degraded in performance by geometric dilution effects.

It is a yet further object of the present invention to provide such a system which may use either DC or AC transmitter excitation techniques and which is insensitive to magnetic objects placed below the transmitter configuration.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
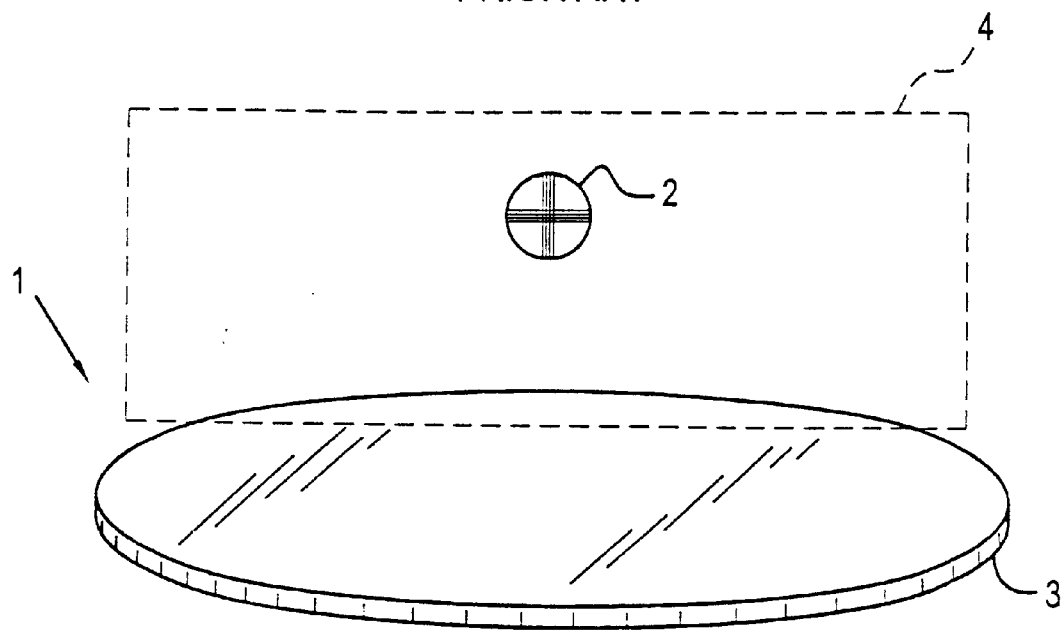
FIG. 1 shows a schematic representation of a prior art system.

With reference, first, to FIG. 1, a system generally designated by the reference numeral 1 is seen to include a prior art three axis dipole transmitter designated by the reference numeral 2 and seen suspended over conductive plate 3. Eddy currents induced in the conductive plate 3 due to the X and Y coils of the transmitter 2 are nearly identical with respect to magnitude, direction and distribution on the conductive plate 3. This similarity causes the eddy current magnetic field vectors at points inside of the operating volume 4 to be quite similar in both magnitude and direction. As the transmitter 2 is moved closer to the conductive plate 3, the magnitudes of the eddy current fields relative to the transmitted fields at any point inside of operating volume 4 will increase. Since the eddy current fields from conductive plate 3 are similar, this causes the total magnetic field vectors from the X and Y coils to become more similar as well, which reduces the angle formed by the intersection of these two vectors. Magnetic dipole systems utilize the angle of intersection of the three distinct vectors from the three orthogonal transmitter coils to derive orientation. If these angles become distorted due to the presence of eddy current fields, the system will output orientation values that are distorted as well.

In order to remove such distortion, in the prior art, such errors are removed using a field mapping process familiar to those skilled in the art. However, such a field mapping process has a serious drawback when applied to a system such as that which is illustrated in FIG. 1. For a given amount of error in determining the three intersection angles, the system will output an error in the orientation output. If this error is due to a noise source, the position and orientation output will become noisy. As the angles of intersection of the transmitted vectors from the X, Y, and Z coils are reduced, receiver position and orientation determination becomes more sensitive to noise and other errors. In the extreme case where they are nearly identical and the angles of intersection are nearly zero, position and orientation determination becomes impossible as sensitivity to errors and noise approaches infinity.

A method of comparing predicted magnetic field distortion levels for a given metallic environment is useful when evaluating different systems. One such method utilizes magnetic field intensity ratios. Such a ratio is defined as the strength of the magnetic field in an area where measurements are to be taken divided by the strength of the magnetic field at an area outside of said area. The latter volume is typically chosen as a volume immediately adjacent to the prior volume. To further facilitate this analysis, a single point is chosen to represent the entire magnetic field within the respective volumes. The theoretical basis for this method follows.

If a conductive object in the regions adjacent to or under the transmitter is subjected to an AC magnetic field, an eddy current will be induced in the object. This induced eddy current will produce a magnetic field component, which, by the addition of vectors, will combine with and distort the normal metal-free magnetic field near the object. The magnitude of this parasitic eddy field is proportional to the magnitude of the AC field near the conductive object.

It is thus seen that if the field vectors in the operating volume above the transmitter assembly remain constant in magnitude and direction while the field magnitude in the regions adjacent to and under the transmitter assembly are reduced, then metallic objects in those regions will have a proportionally reduced distorting effect on the field in the operating volume above the transmitter assembly. If the field magnitude in the operating volume above the transmitter assembly is increased while the field magnitudes in the regions adjacent to and under the transmitter assembly remain constant, the distortion reducing effect is similar. Accordingly, the ratio of the magnetic field amplitude in the operating region above the transmitter assembly over that of the regions adjacent to and under the transmitter assembly may be used to predict sensitivity to metallic objects. A similar description applies to ferromagnetic distortion effects when the distorting objects are located in the regions adjacent to and below the transmitter assembly.

Figure 5:
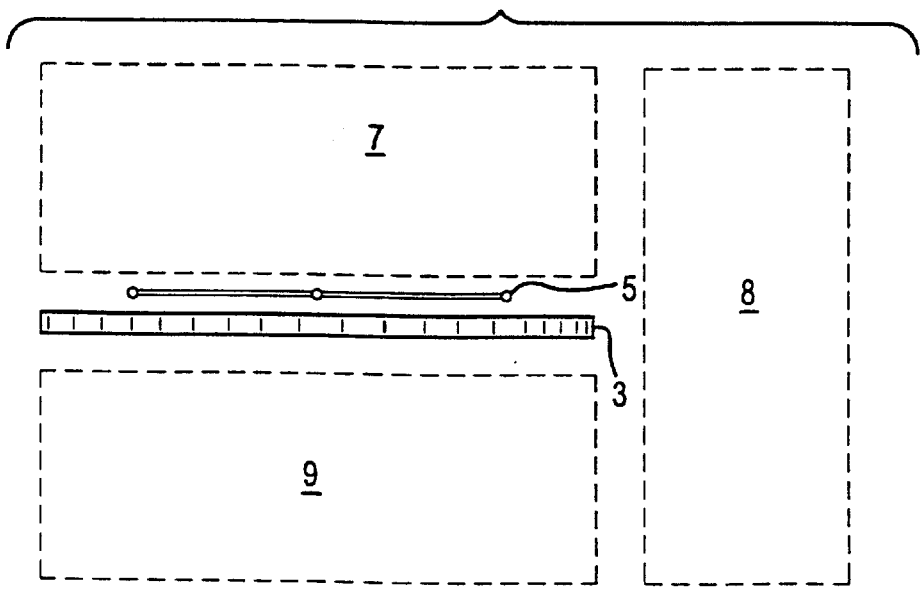
FIG. 5 shows the magnetic flux pattern of a prior art non-dipole transmitter placed over a conducting ground plane.
Figure 13:
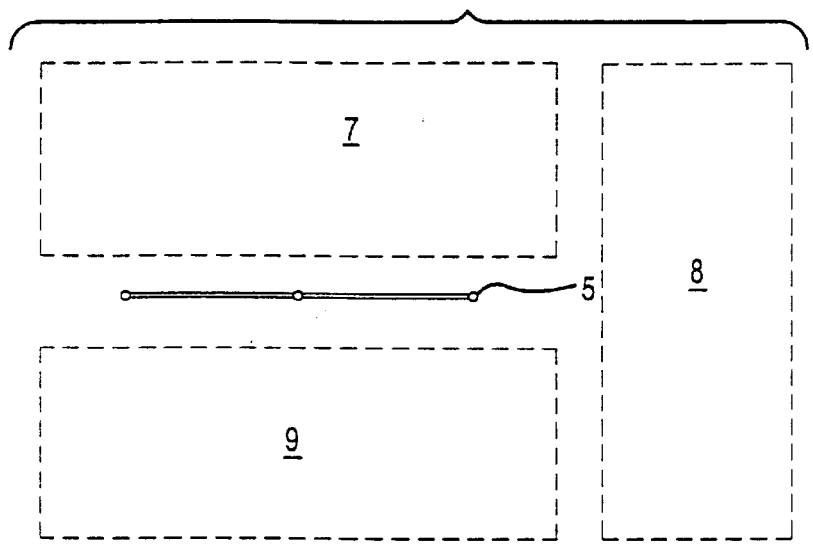
FIG. 13 shows the magnetic flux pattern of a prior art non-dipole transmitter loop in free space.

If the relative magnetic distortion sensitivity values of a single transmit coil in the configuration such as is shown in FIG. 13, can be established as a normal value, then a relative distortion sensitivity figure of merit designated Ma may be arrived at where Ma equals (the field of the system depicted in FIG. 2 in the region above the transmitter assembly) divided by (the field of the system depicted in FIG. 5 in the region above the transmitter assembly) divided by (the field of the system illustrated in FIG. 2 in the region adjacent the transmitter assembly) divided by (the field of the system in the configuration of FIG. 5 in the region adjacent the transmitter assembly). The system depicted in FIG. 11 will have a sensitivity figure of merit of 1 in that FIG. 11 will, for example, be chosen as the reference system.

Similarly, for comparison of objects below the transmitter assembly, we can define a term Mb which equals (the field of the system of FIG. 2 in the region above the transmitter assembly) divided by (the field of the system illustrated in FIG. 5 in the region above the transmitter assembly) divided by (the field of the system of FIG. 2 below the transmitter assembly) divided by (the field of the system of FIG. 5 in the region below the transmitter assembly). Using the figures of merit Ma and Mb, several different configurations can be evaluated to determine likely relative sensitivities to metallic objects in the regions adjacent to and below the transmitter assembly.

With reference to FIG. 13, a further prior art system is shown wherein a single turn transmit coil 6 having a diameter of 7.5 inches operates at a frequency of 20 KHz and with a current of 1 ampere rms. The magnetic field vectors may be calculated using a number of methods, one of which is known as the so-called finite element method. The primary tool for this calculation is a software program employing Maxwell's equations as boundary conditions and field properties. Using a computerized drafting program, the model to be analyzed is created. The model consists of both the geometry and material properties of the system, as well as any excitation properties. This model is then operated on by a numerical finite element solver, which simulates the behavior of electromagnetic fields in and around the model. The result is an accurate, quantified value for the magnetic filed at all points of the model. By judicious creation of the models, easily accomplished by those skilled in the art, it is possible to analyze various combinations of materials and geometry. It is further possible to choose an exact spatial location on the model and obtain an accurate numerical figure for the magnetic field vector magnitude and direction at that location. By choosing these same locations and varying model parameters, it is possible to view the effects of material properties and geometries on the magnetic field at a particular spatial location. Utilizing this method, the magnetic field vector magnitudes for operating volume 7 are (9.12e–17 Tesla), the adjacent space 8 is (7.2e–17 T) and the region 9 below the transmit coil 6 is (6.4e–15 T). This configuration is chosen as a reference configuration and, accordingly, Ma and Mb are equal to 1.

With reference, now, to FIG. 5, a further prior art system is shown in which a flat transmitter 5 is suspended 0.3 inches over the conductive plate 3. In this prior art teaching, the conductive plate 3 is approximately 0.25 inches thick and made from aluminum. Thus, the overall height from the top surface of the conductive plate 3 to the top of the transmitter 5 is 0.55 inches.

In comparing the configurations of FIGS. 5 and 13, looking at the configuration of FIG. 5, compared with the field levels of the configuration of FIG. 13, the operating volume field 7 is reduced to 27%, adjacent space 8 has been reduced to 40%, and the region 9 below the conductive plate 3 has been reduced to 0.14%. From this data, it can be concluded that Ma equals 0.68 and Mb equals 193. A value of Ma equals 0.68 indicates that this system is likely to experience greater distortion due to metallic objects within the region 8. The Mb value indicates that the system will be quite insensitive to metallic objects located below the conductive plate 3 within the region 9. A serious disadvantage in the configuration of FIG. 5 is that the field operating volume 7 has been reduced to 27% of its original value. This means that for a given noise level in the tracking system and its environment, position output will necessarily be degraded. Increasing transmitter current by a factor of 3.6 can compensate for this loss, but this will result in a more robust and costly drive system.

Also, if the transmit loop 5 is not a superconductor, it will dissipate power equal to $I^2R$ or 12.9 times more power for a given transmit loop configuration. This may require a larger conductor size and/or provisions to remove heat from the conductor of transmit loop 5, both of which provide distinct disadvantages. The system described in FIG. 5 also suffers from substantial geometric dilution effects due to similar eddy current fields from conductive plate 3 when any of the three transmit loops are energized. Thus, the conductive plate 3 is more sensitive to metallic objects inside of operating volume 7.

Figure 2:
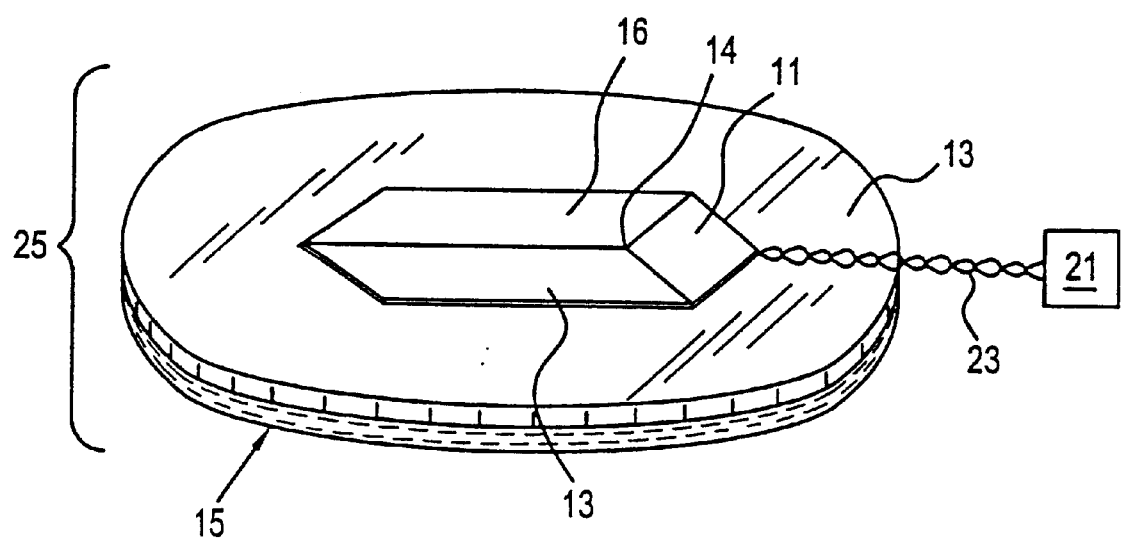
FIG. 2 shows a perspective view of a preferred embodiment of the present invention with the rhombic transmitter being shown schematically.
Figure 3:
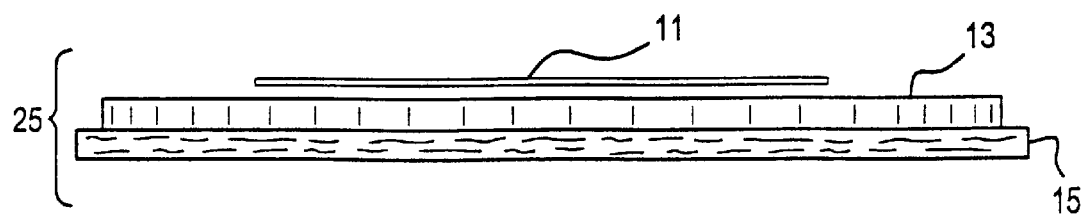
FIG. 3 shows a side view of the preferred embodiment illustrated in FIG. 2.
Figure 4:
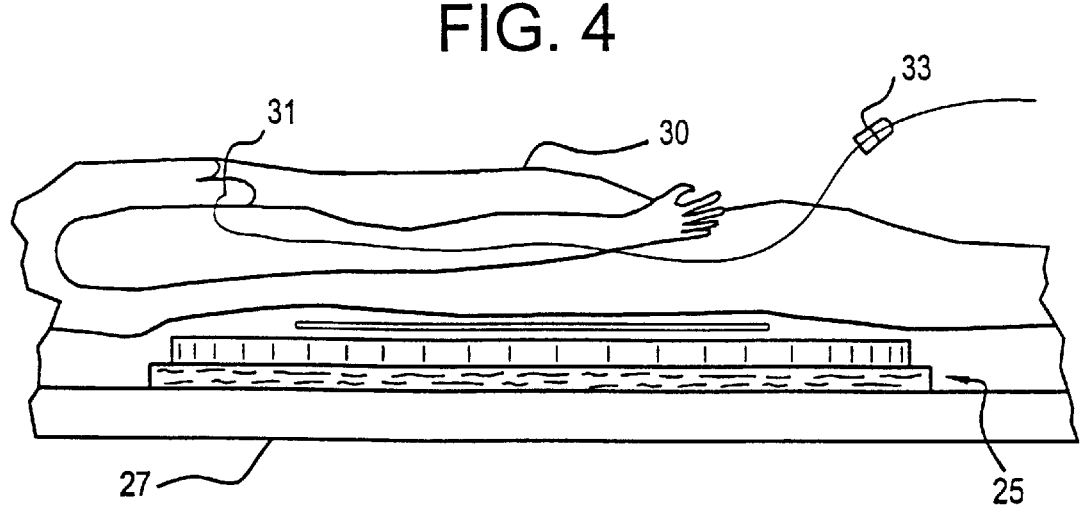
FIG. 4 shows a side perspective view of the preferred embodiment of FIGS. 2–3, also showing a patient supported above the preferred embodiment on an operating table.

With reference, now, to FIGS. 2, 3 and 4, one embodiment of the present invention is generally designated by the reference numeral 10 and is seen to include a planar rhombic transmitter 11 located over a permeable attenuator 13 mounted on top of a conductive plate 15.

In this embodiment, the transmitter 11 consists of a PC board having the three axis transmitter etched onto the surface thereof.

For proper operation, the permeable attenuator should not be a major source of eddy current field. For a given material having a bulk resistivity p, as the frequency is decreased a point is reached where the eddy current in the material is reduced to the point where the distortion to the incident magnetic field becomes small. In the extreme case of a DC transmitter, it can be seen that the conductivity of the permeable attenuator is not of concern. It is apparent that there is a relationship between material conductivity and frequency which is of use when determining the frequency of operation of the transmitter and also when selecting the required bulk resistivity of the permeable attenuator. This can be described by the bulk resistivity p of the material in ohm meters divided by the frequency of operation f of the transmitter, defined as Rfc=p/f. For steels, when Rfc is greater than about 2e–10, the parasitic eddy current field from the permeable attenuator is low enough such that it is beneficial to use the steel attenuator versus an aluminum or copper ground plane. For cold rolled steel, this occurs at a transmit frequency of about 500 Hz. When Rfc is greater than 2e–9, it is generally beneficial to use steel or stainless steel over ferrite unless it is absolutely required to fully optimize the transmit field characteristics. For cold rolled steel, this occurs at a transmit frequency of about 50 Hz. When Rfc is greater than 1e–8, the attenuator is acting as an essentially pure permeable attenuator when the material is steel or stainless steel. For cold rolled steel, the transmitter frequency would be 10 Hz. In this case, replacing the inexpensive and strong steel with expensive and fragile ferrite would produce no performance improvement.

The permeable attenuator 13 may be as thin as 0.001 inches in thickness. The thickness of the permeable attenuator is generally chosen such that the saturation flux density of the attenuator material is not exceeded. Some ferrites have a saturation flux density of a few hundred Gauss, while annealed iron materials have about 15,000 Gauss. Mumetal has a saturation flux density of about 7,000 Gauss. Analyzing the attenuator thickness combined with a transmitter means using finite element analysis will produce values for flux density within the attenuator. For relatively thin attenuators, flux density is inversely proportional to thickness, so if the density is seen to be at or near saturation, the attenuator can be made thicker. In other cases, the transmitter excitation may be reduced. If the flux density within the attenuator exceeds the saturation value, the shielding effect of the attenuator is reduced. In some applications in which cost or weight is placed at a premium, operation with a saturated attenuator may still be acceptable, as the attenuator will still exhibit reduced sensitivity to metallic objects adjacent to and below the transmitter compared to a non-attenuator equipped system. The permeable attenuator 13 may be made of a highly permeable but substantially non-conductive material. One such material is ferrite. This material has a relative permeability range of 50 to 25,000 compared with the permeability of air. This material has a typical resistivity on the order of 0.1 Ohm/meter to 10^8 Ohm/meter, depending on the commercial formulation used. In a specific implementation of the preferred embodiment, a suitable material may be ferrite type MN67 which has a resistivity of 25 degrees C. of 10^4 Ohms/meter and a relative permeability of 2500 at 25 degrees C. The material is 0.2 inches thick and 18 inches in diameter and is concentric about the transmitter 11 formed by three rhombic transmit loops 14, 16 and 18. As seen in FIG. 2, a transmit driver 21 is connected to the transmitter 11 via an electrical conductor 23. The driver 21 sequentially energizes each of the loops of the transmitter 11 with a one ampere r.m.s. at a frequency of 20 Khz. A further material to be employed for the permeable attenuator is mumetal. This material is a Nickel Iron alloy containing small amounts of other metals. It is specially formulated and annealed to provide a relative permeability Ur of 75,000 to 300,000, although technically conductive the enhanced permeability over that of ferrite compensates for this aspect and the mumetal has proven to be a highly effective permeable attenuator. A representative commercial product is named AD-MU-80 mumetal, and is made by Advance Magnetics, Inc. In an experiment, a 0.010 inch thick sheet of this material was employed as the permeable attenuator 13 and the effects on the magnetic field of the transmitter were analyzed. It was found that at transmitter frequencies of DC to 3 KHz, AD-MU-80 mumetal provided performance substantially equal to that of the 0.2 inch thick MN-67 ferrite material. At frequencies from 3 KHz to 19 KHz, AD-MU-80 mumetal provided the same percentage reduction in adjacent field strength and below field strength as MN-67 ferrite, but provided less of a field strength increase in the operating region. At frequencies above 19 KHz, AD-MU-80 mumetal provided the same field reductions in the below and adjacent regions as MN-67 ferrite, but also reduced the field strength in the operating region. At all frequencies tested, which include DC and 5 MHz, AD-MU-80 mumetal produced significantly lower vector dilution effects and significantly higher transmitter field strength in the operating region than a conductive ground plane.

Mumetal has mechanical properties that are very useful as compared to ferrite. Since it typically has about 30 times the permeability of ferrite at frequencies below a few Khz, it can be made much thinner than ferrite while performing equally well as a permeable attenuator. Unlike ferrite, mumetal is not a brittle ceramic material but is instead a ductile metal. This allows the rigid support backing required for ferrite to become comparatively thin or non-existent, as mumetal will not fracture when stressed as will ferrite. Since the permeable attenuator 13 may be made thinner, a weight savings may be realized over ferrite, with obvious benefits. Also, mumetal is much less expensive than ferrite, and may easily be shaped, formed, machined, and welded into convenient shapes to form the permeable attenuator 13. As a result of these additional benefits, mumetal may be useful in replacing ferrite as the permeable attenuator 13 even in cases where it provides lower performance gains, as economic and mechanical considerations may offset the performance difference.

The conductive plate 15 is optional and is located directly below and substantially in contact with the permeable attenuator 13. In one embodiment, the conductive plate 15 is made of aluminum alloy 6061 T-6 and has a thickness of approximately 0.1875 to 0.25 inches.

Thus, the combination of the transmitter 11, permeable attenuator 13, and conductive plate 15, in the embodiment shown, has a combined thickness of approximately 0.3 to 0.625 inches, a quite compact assembly. The combination of the transmitter 11, permeable attenuator 13, and conductive plate 15 may be generally referred to as transmitter assembly 25.

FIG. 4 shows the transmitter assembly 25 mounted on a surgical table 27 with a patient 30 lying on the transmitter assembly 25. A receiver 31 has been inserted into the body of the patient 30 and receives signals from the transmitter assembly 25 conveying them to a computer (not shown) via the electrical conductor 33 so that the position and orientation of the receiver 31 may be accurately determined.

Figure 16:
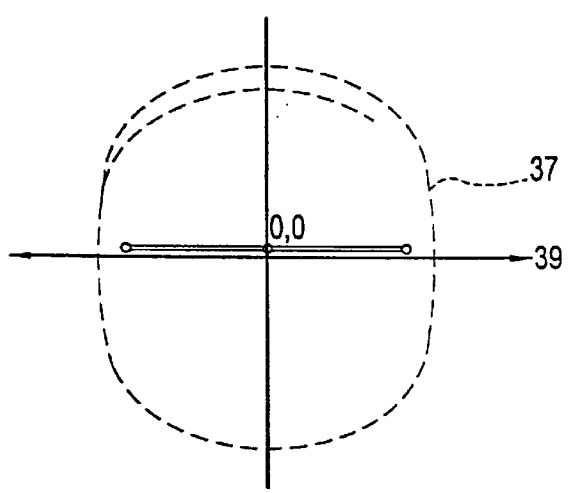
FIG. 16 shows a graph of a magnetic field extending above and below a reference line as generated at the point 0, 0.
Figure 17:
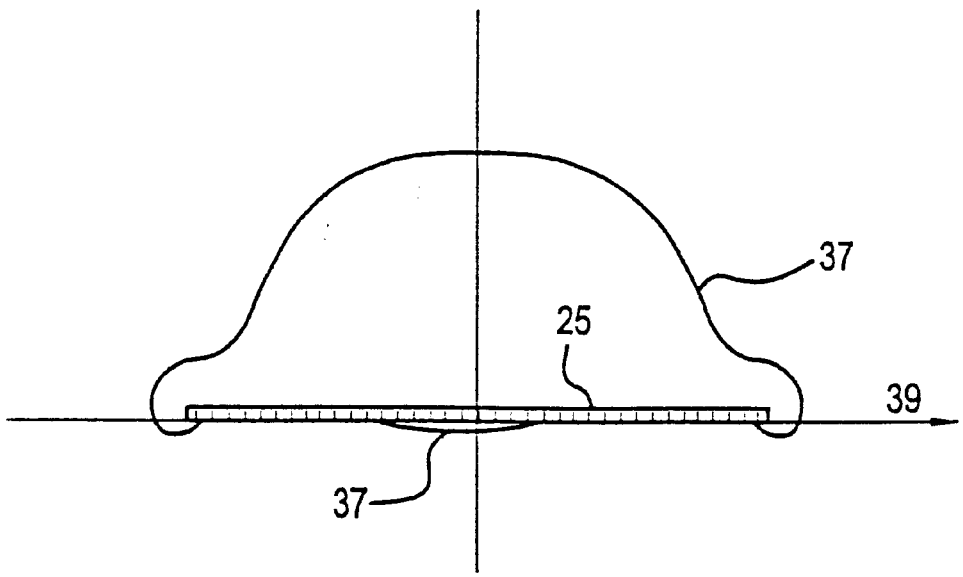
FIG. 17 shows a graph of the same magnetic field shown in FIG. 16 truncated below the reference line through employment of a permeable attenuator.
Figure 18:
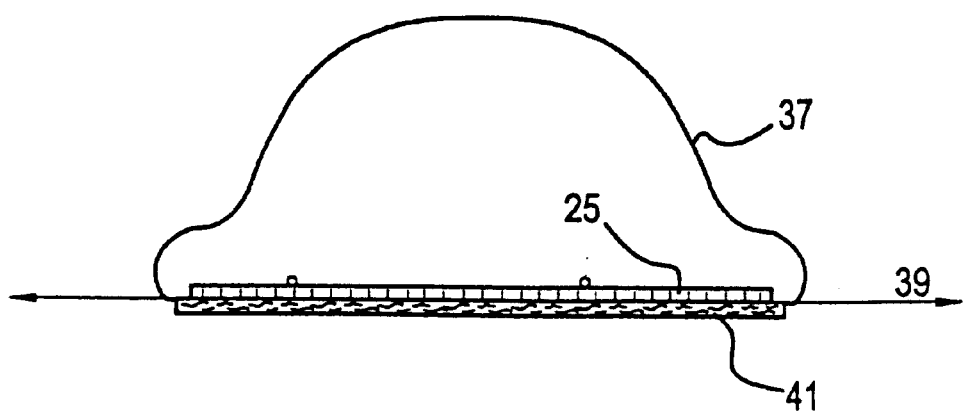
FIG. 18 shows a graph of the same magnetic field shown in FIG. 17 but further truncated through addition of a conductive plate.

FIG. 16 shows a graph of a magnetic field 37 emanating from the point 0, 0 with the field extending above and below the x-axis line 39. By contrast, with reference to FIG. 17, when a permeable attenuator 25 is placed on the line 39, the magnetic field 37 is changed in shape so that virtually none of the field 37 extends below the line 39. FIG. 18 shows further attenuation of the field 37 through addition of conductive plate 41 below permeable attenuator 25. This effect is what occurs through operation of the preferred embodiment illustrated in FIGS. 2, 3 and 4.

Figure 6:
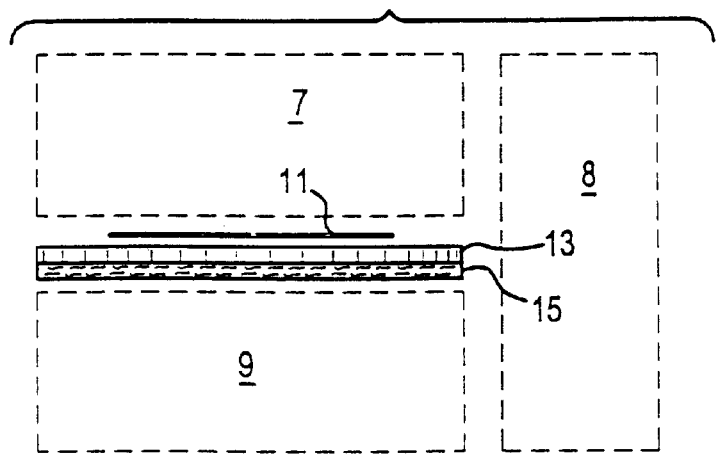
FIG. 6 shows a magnetic flux pattern of the invention illustrated in FIGS. 2–4.

With reference to FIG. 6, an embodiment of the transmitter assembly 25 is shown wherein the transmitter 11 is located directly on top of a ferrite layer 13 made of MN67 ferrite material 0.2 inches thick, which ferrite layer 13 lies directly on top of a 0.25 inch thick aluminum conductive plate 15. Compared to the field levels exhibited with reference to FIG. 13 as described above, the operating volume 7 is 159% of that of FIG. 13, the adjacent space 8 is 60% of that of FIG. 13, and the region 9 below the transmitter assembly 25 is 0.11% of that of FIG. 13. From these results, it is clear that Ma equals 2.65 and Mb equals 1445. Thus, it should be understood that the configuration of FIG. 6 performs better than the systems of FIGS. 13 and 5 with respect to predicted sensitivity to metallic objects in the regions 8 and 9. The signal level is also increased within the operating volume 7 by 151% as compared to FIG. 13.

Figure 7:
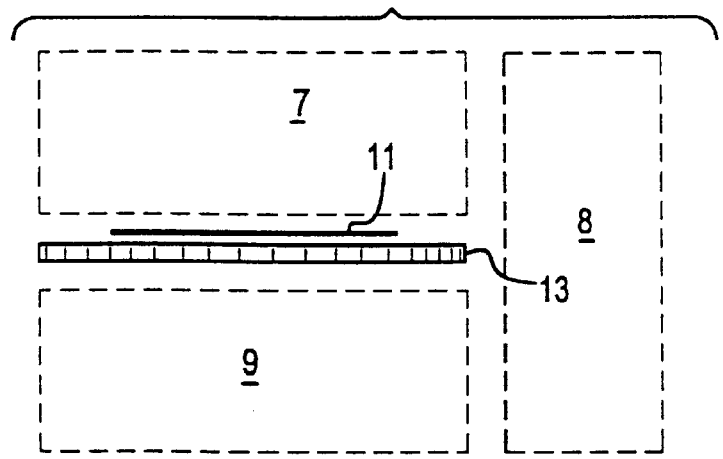
FIG. 7 shows the magnetic flux pattern of the transmitter as depicted in FIG. 3 but without the conductive material plate under the permeable attenuator.

FIG. 7 depicts the transmitter 11 located directly on top of the ferrite plate 13 with the ferrite plate being 0.2 inches thick and being composed of type MN67 ferrite. No conductive plate is employed as is also the case in the embodiments of FIGS. 8–12. The overall thickness of the transmitter assembly in FIG. 7 is 0.2 inches. Compared to the field levels of FIG. 13, the operating volume field 7 is 191%, the adjacent space 8 is 81% and the region within and under the table 9 is 4.3%. It follows from this data that Ma equals 2.35 and Mb equals 44.4. From this data, it is predicted that this system will be significantly less sensitive to metallic objects in the region 8 and much less sensitive to metallic objects in the region 9 as compared to FIG. 13. Also, the field in operating volume 7 has been increased by 191% over the original which will result in improved signal-to-noise performance. Vector dilution is negligible. Although the signal level in operating volume is only 83% of that of FIG. 7, the FIG. 6 system is, in practice, much better suited to applications where the region 9 consists of the region within and below the operating table since the system will not experience significant magnetic field distortion in the region 7 when the composition of the region 9 is varied. Vector dilution is negligible so that sensitivity to metallic objects within the operating volume 7 is not diminished over FIG.

13. Of course, it is stressed that the present invention may effectively operate without the conductive plate under certain circumstances. In the case of DC transmitter excitation, for example, the additional shielding effect of the conductive plate is reduced to insignificant levels. In certain other cases, the performance benefit of the conductive plate may be outweighed by reduced mass, thickness, or other system considerations. In cases such as these, the additional mechanical support provided by the conductive plate may also be unnecessary, so that the conductive plate is removed entirely. In cases where the conductive plate provides a performance benefit to the system, this benefit is always of a secondary nature, with the primary performance enhancement arising from the permeable attenuator.

TABLE 1

Comparison of Ma, Mb an operating Volume Magnetic Field Strength for 4 Representative Planar Non-Dipole Magnetic Transmitters

| SYSTEM OF | Ma | Mb | Operating Volume Magnetic Field Referenced to that Of FIG. 13 |
|---|---|---|---|
| FIG. 13 | 1 | 1 | 1 |
| FIG. 5 | .68 | 193 | .27 |
| FIG. 6 | 2.65 | 1445 | 1.59 |
| FIG. 7 | 2.35 | 44.4 | 1.91 |

A benefit of the conductive plate 15 is that it provides a physical mechanical support to the ferrite layer 13 which is typically quite fragile. Of course, additionally, undesirable signal loss effects of the eddy current effects from conductive plate 15 are substantially eliminated. Where used, the conductive plate 15 is chosen to be several skin-depths thick at the frequency of operation to provide a maximum degree of field attenuation at the bottom of the transmitter configuration 25. In the case of very low frequency excitation, including DC excitation, where skin depths become very large, the purpose for the conductive plate 15 becomes purely for mechanical support of the transmitter.

Applicant has found that a non-dipole system may be enhanced in performance through operation of the present invention. The enhanced non-dipole shows increased magnetic field strength within the operating volume with an accompanying decrease in output noise.

It is, in a practical sense, totally insensitive to metallic objects located beneath the transmitter, for example, in the region designated by the reference numeral 9. Such a system shows reduced sensitivity to metallic objects adjacent to the operating volume and also has reduced vector dilution effects as compared to a ground plane-based shielding method and is thus inherently less sensitive to metallic objects within the operating volume and also less sensitive to noise.

Figure 8:
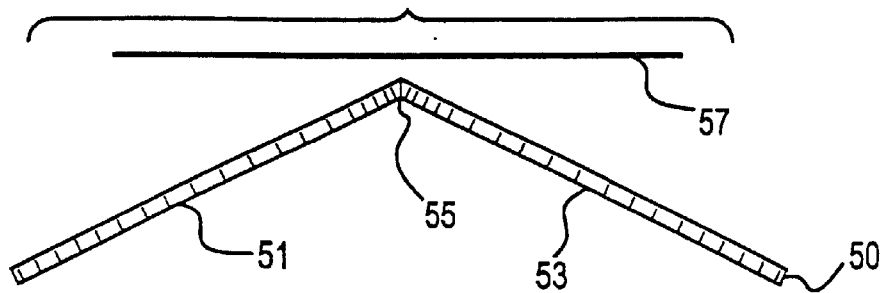
FIG. 8 shows a modification of the present invention employing a non-planar, permeable attenuator.

FIG. 8 shows an alternative permeable attenuator 50 that is non-planar in configuration having a shallow V-shaped cross-section, consisting of two portions 51 and 53 meeting at a line of intersection 55. The portions 51 and 53 make an angle of 15 degrees with respect to horizontal and angle downwardly from a central upper terminus. The transmitter 57 is suspended thereabove as shown in FIG. 8.

Figure 9:
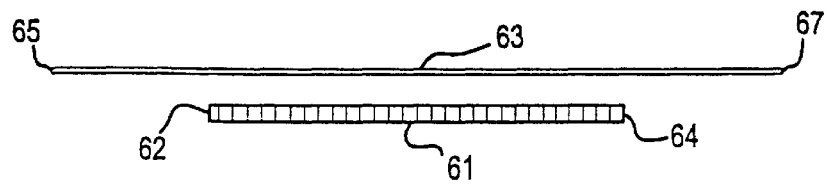
FIG. 9 shows the magnetic flux pattern from a further modification wherein the transmitter extends beyond the periphery of the permeable attenuator.

FIG. 9 shows a further embodiment of the present invention designated by the reference numeral 60 wherein the permeable attenuator 61 has a transmitter 63 suspended thereover with the peripheral edges 65, 67 of the transmitter 63 overlying the peripheral edges 62 and 64 of the permeable attenuator 61.

Figure 10:
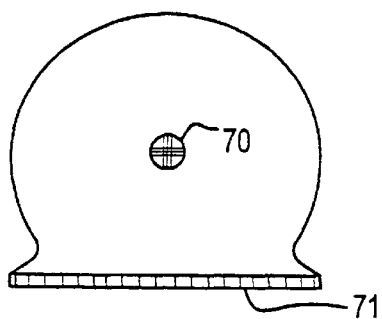
FIG. 10 shows the magnetic flux pattern wherein the transmitter comprises a dipole transmitter.

FIG. 10 shows a transmitter 70 suspended above a permeable attenuator 71 and depicts the magnetic flux pattern for this configuration.

Figure 11:
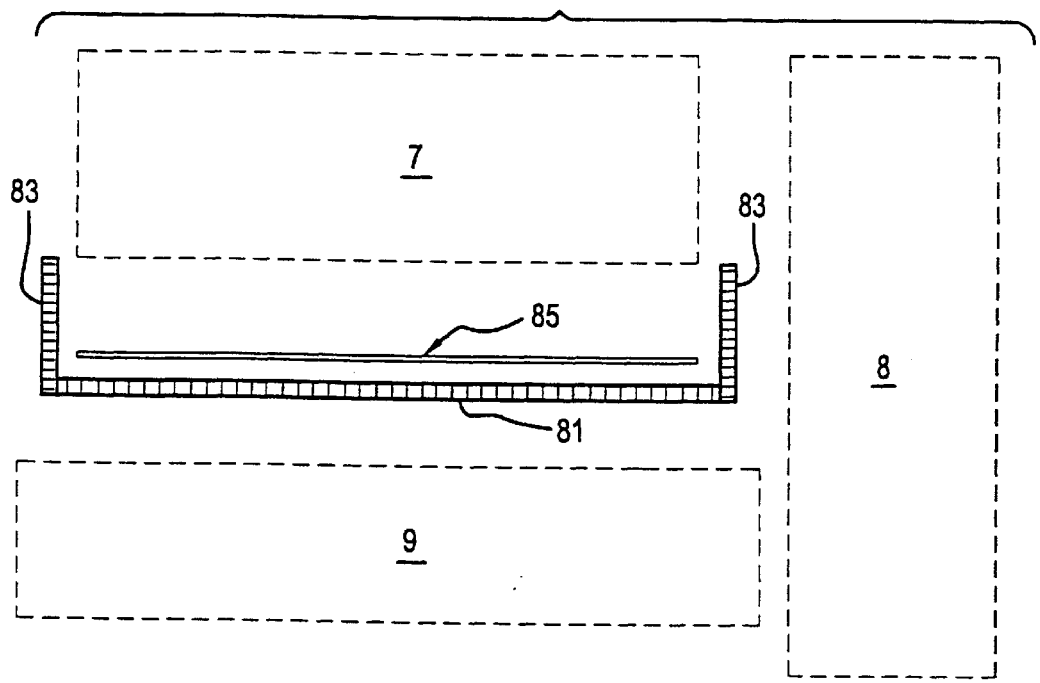
FIG. 11 shows the magnetic flux pattern in a modification of the permeable attenuator wherein the periphery has raised edges.

FIG. 11 shows a system 80 having a permeable attenuator 81 with upturned peripheral edges 83 so that the cross-section thereof resembles a cake pan. The transmitter 85 is suspended within the volume created by the peripheral edges 83. Applicant has found that when using a permeable attenuator such as that which is depicted by the reference numeral 81, the magnetic field concentrates about the upper edges thereof, providing certain advantages when the configuration is placed on a ferromagnetic sheet, such as plate steel. The advantage of a thin transmitter is somewhat compromised in this case and the field shape around the raised peripheral edges 83 is also changed as is the intensity distribution.

Figure 15:
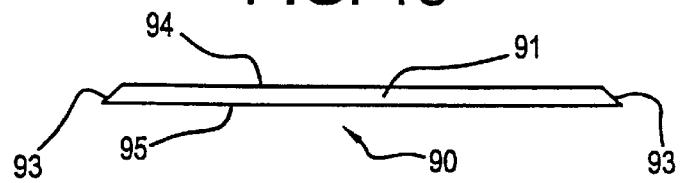
FIG. 15 shows a modification of the permeable attenuator having peripheral edges that taper outwardly from a top surface thereof to a bottom surface thereof.

In a further modification, reference is made to FIG. 15 which shows a permeable attenuator 90 having a main body 91 and peripheral edges 93 that are tapered outwardly from a top surface 94 to a bottom surface 95 of the attenuator 91. The peripheral edges 93 make an angle that is preferably in the range of 30 to 85 degrees. As the angle reduces, the performance results improve, however, one arrives at the point of diminishing returns as the angle is reduced for two reasons. First, it becomes more and more difficult to manufacture the attenuator 91 with the shallower angled peripheral edges 93. Furthermore, once one reduces the angle of the peripheral edges from the typical 90 degrees to 45 degrees, one has achieved about 99% of the enhancement that is possible to achieve. Using such an angled peripheral edge reduces the extent of the "hump" of the field at the edge. The bevel of the angled peripheral edge 93 moves distortions closer to the edge of the permeable attenuator 91 and further downward into, for example, the operating table adjacent the inventive system.

Figure 12:
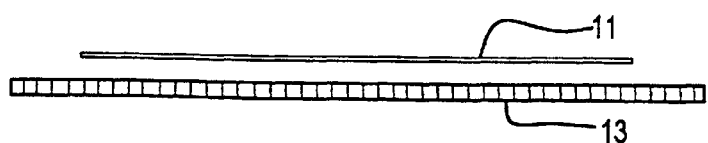
FIG. 12 shows the magnetic flux pattern from a further variation wherein the transmitter is raised above the permeable attenuator.

FIG. 12 shows a further modification of the assembly illustrated in FIGS. 2–4 in which the transmitter coils 11 are suspended above the permeable attenuator 13.

Figure 14:
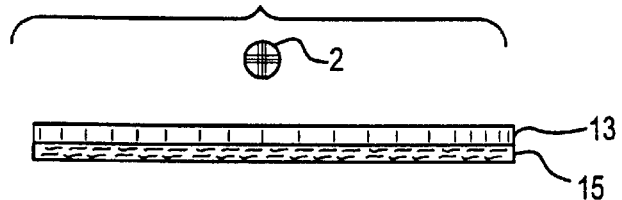
FIG. 14 depicts the system wherein a dipole magnetic transmitter is located above a permeable attenuator.

FIG. 14 depicts the fact that use of the permeable attenuator 13 reduces geometric dilution effects of the ground plane by providing a low reluctance flux path for the magnetic field emitted by the transmitter. This effectively attenuates the magnetic field which is incident upon the conductive plate 15 to an insignificant level with the result that geometric dilution effects are greatly reduced while maintenance of insensitivity to metallic objects below the transmitter occurs. While the permeable attenuator 13 distorts the transmitted fields from the X, Y, and Z coils, the distortion is not severe and is easily removed using field mapping techniques.

Applicant has found that use of the permeable attenuator, with its extremely low reluctance, causes the magnetic field to travel primarily through the low reluctance path provided by the permeable material effectively shielding objects below the permeable material. The advantages of the use of mumetal for the permeable attenuator have been explained in detail hereinabove.

Use of aluminum for the conductive plate, where a conductive plate is employed, is advantageous because aluminum attenuates the magnetic field in addition to providing a support for the brittle ferrite permeable attenuator. Applicant has found that the ferrite or mumetal permeable attenuator provides 95% of the benefit of the present invention with modifications and variations disclosed herein providing the other 5% of the benefit, to wit, such things as the shape of the periphery of the permeable attenuator and the use of the aluminum conductive plate.

One typical application intended for the present invention is on top of an operating table. Operating tables have a lot of steel in them and are heavily cantilevered. The present invention amplifies the field in the operating region above the table and reduces the field next to the transmitter and below the top surface of the operating table.

If desired, the transmitter 11, permeable attenuator 13, and aluminum conductive plate 15, where used, may be laminated together with a material such as silicon or epoxy adhesive. As mentioned above, the finished laminated assembly may have a thickness no greater than 5/8 of an inch making it a convenient enhancement to any operating room.

As such, an invention has been disclosed in terms of preferred embodiments thereof which fulfill each and every one of the objects of the invention as set forth hereinabove and provide a new and useful magnetic position measurement system with field containment means of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. In a magnetic position measurement system, the improvement comprising means for containing a magnetic field used to conduct measurements of position of an object in at least three dimensions, said containing means comprising a magnetic field permeable attenuator located adjacent a region where position of said object in three dimensions is being measured by a magnetic field, said attenuator attenuating said magnetic field on a side of said attenuator remote from said region, said system including transmitter means for engaging said attenuator on a side thereof opposite said remote side, a number of transmit axes multiplied by a number of receive axes being at least equal to a desired number of measured degrees of freedom.

2. The system of claim 1, wherein said attenuator is flat.

3. The system of claim 2, wherein said attenuator has a uniform thickness of 0.01 to 0.25 inches.

4. The system of claim 3, wherein said attenuator is made of a material chosen from the group consisting of ferrite and mumetal.

5. The system of claim 4, wherein said attenuator has an upraised peripheral edge.

6. The system of claim 2, wherein said attenuator has an upraised peripheral edge.

7. The system of claim 2, wherein said attenuator has a peripheral edge tapered outwardly from a top surface of said attenuator to a bottom surface thereof.

8. The system of claim 4, wherein said attenuator has a peripheral edge tapered outwardly from a top surface of said attenuator to a bottom surface thereof.

9. The system of claim 1, wherein said attenuator has a V-shaped cross-section.

10. The system of claim 9, wherein said attenuator has a uniform thickness of 0.01 to 0.25 inches.

11. The system of claim 10, wherein said attenuator is made of ferrite.

12. The system of claim 10, wherein said attenuator is made of mumetal.

13. The system of claim 1, further including a conductive plate attached under said attenuator.

14. The system of claim 13, wherein said plate has a thickness of 0.1875 to 0.25 inches.

15. The system of claim 14, wherein said plate is made of non-ferrous metal.

16. The system of claim 14, wherein said plate is made of a conductive metal.

17. The system of claim 16, wherein said conductive metal is non-ferrous.

18. The system of claim 1, further wherein said transmitter means is mounted on top of said attenuator.

19. The system of claim 18, wherein said transmitter means comprises a PC board with said transmitters etched thereon.

20. The system of claim 19, wherein said PC board is 0.03125 to 0.125 inches thick.

21. The system of claim 3, wherein said magnetic field is created by a pulsed DC power source.

22. A magnetic position measurement system, comprising:
    a) a magnetic field permeable attenuator;
    b) a transmitter means above said attenuator for measuring in three dimensions;
    c) said transmitter means and attenuator being laminated together.

23. The system of claim 22, wherein said transmitter means and attenuator have a combined thickness of 0.08 to 0.375 inches.

24. The system of claim 22, wherein said transmitter means comprises a PC board with a transmitting means etched thereon.

25. The system of claim 22, wherein said attenuator is made of a material chosen from the group consisting of ferrite and mumetal.

26. The system of claim 22, further including a conductive plate under said attenuator.

27. A method of measuring position of an object in a prescribed three dimensional space including the steps of:
    a) defining a three dimensional space;
    b) locating a magnetic field permeable attenuator adjacent said space;
    c) placing transmitter means on a side of said attenuator facing said space, a number of transmit axes multiplied by a number of receive axes being at least equal to a desired number of measured degrees of freedom;
    d) operating said transmitter means; and
    e) measuring position of said object.

28. The method of claim 27, wherein said locating step includes the step of providing an attenuator with a uniform thickness of 0.01 to 0.25 inches.

29. The method of claim 28, wherein said providing step includes the step of making said attenuator of one of ferrite or numetal.

30. The method of claim 27, further including the step of installing a conductive plate under said attenuator.

31. The method of claim 30, wherein said installing step includes installing a conductive plate made of aluminum.

32. The method of claim 30, wherein said installing step includes installing a conductive plate having a thickness of 0.1875 to 0.25 inches.

33. The method of claim 30, further including the step of laminating together said transmitter means, attenuator and plate.

* * * * *